United States Patent [19]

Cronshaw

[11] Patent Number: 4,471,649
[45] Date of Patent: Sep. 18, 1984

[54] PERMEABILITY MONITORING OF SHEET MATERIALS

[75] Inventor: Arnold W. Cronshaw, Eastleigh, England

[73] Assignee: British-American Tobacco Company Limited, London, England

[21] Appl. No.: 348,448

[22] Filed: Feb. 12, 1982

[30] Foreign Application Priority Data

Feb. 20, 1981 [GB] United Kingdom ............... 8105351

[51] Int. Cl.$^3$ .............................................. G01N 15/08
[52] U.S. Cl. ....................................................... 73/38
[58] Field of Search .................... 73/38, 37.7, 159, 160

[56] References Cited

U.S. PATENT DOCUMENTS

| | | | |
|---|---|---|---|
| 3,498,109 | 3/1970 | Steptoe et al. | 73/37.7 |
| 3,720,095 | 3/1973 | Molins | 73/38 |
| 4,050,291 | 9/1977 | Nelson | 73/38 |
| 4,311,037 | 1/1982 | Gotchel et al. | 73/38 |
| 4,348,887 | 9/1982 | Lorenz et al. | 73/38 |

FOREIGN PATENT DOCUMENTS 2001444  1/1979  United Kingdom ................. 73/38

Primary Examiner—Stephen A. Kreitman
Attorney, Agent, or Firm—Kane, Dalsimer, Kane, Sullivan and Kurucz

[57] ABSTRACT

A device or method for monitoring the gas-permeability of a sheet material is disclosed. The device comprises a first gas-flow chamber having an inlet, which, during operation of the device is closed by the sheet material extending across the inlet. A second flow chamber has an outlet by which a gaseous medium can be directed towards the sheet material with a leakage path whereby a significantly greater proportion, suitably 90%, of the gas-flow in the second flow chamber is permitted to leak to the atmosphere. This leakage path is provided by spacing the gas outlet of the second chamber from the position in which the sheet material extends across the gas inlet of the first chamber. A measurement means, preferably a pressure transducer is connected across a low-impedance laminar-flow device.

10 Claims, 2 Drawing Figures

PERMEABILITY MONITORING OF SHEET MATERIALS

BACKGROUND OF THE INVENTION

1. Field of the Invention

This invention concerns improvements relating to the monitoring or determination of the permeability of sheet materials, particularly but not exclusively webs of paper used in the tobacco industry.

2. Brief Description of the Prior Art

In United Kingdom Patent Specification No. 1,239,408, it has been proposed that, in the manufacturing of cigarettes, the permeability of a web of cigarette paper should be monitored continuously for the purpose of identifying any portions of the web which are unsatisfactory. A device disclosed in that specification for monitoring paper web comprises a suction chamber disposed in contact with one side of the web and a second chamber disposed in contact with the other side thereof. A bleed hole communicates with the second chamber, whereby ambient air may flow into the second chamber when a partial vacuum is established in the suction chamber. Pressure indicating means is operative to measure the pressure in the second chamber, the pressure therein varying in accordance with variations in the permeability of the web which is conveyed between the two chambers. The use of the partial vacuum is disadvantageous in that paper dust and other debris are likely to be sucked into and cause malfunctioning of the device. The monitoring device of the aforesaid Specification also has the disadvantage that both chambers have to be maintained in contact with respective sides of the web in order to produce necessary hermetic seals therewith.

To our knowledge, there is no device currently available which adequately meets the practical requirements for continuous on-line monitoring of paper webs of the tobacco industry, such webs including, for example, webs of tipping, filter-plug wrapping and cigarette wrapping material.

SUMMARY OF THE INVENTION

It is an object of the present invention to provide a monitoring device which does meet the above-mentioned requirements.

The invention provides a device for monitoring the gas permeability of a sheet material comprising a first flow chamber having an inlet which, during operation of the device, is closed by the sheet material extending across said inlet, gas-measurement means operable to measure gas flow or gas pressure in said first flow chamber, and a second flow chamber having an outlet whereby a gaseous medium, suitably air, may be directed towards said sheet material, there being provided a gas-leakage path whereby a significantly greater proportion of the gas flow in said second flow chamber is permitted to leak to atmosphere than that proportion which passes through said sheet material into said first flow chamber.

The gas leakage path is preferably provided by the simple expedient of spacing the outlet of the second flow chamber from the position occupied by sheet material when the sheet material extends across the inlet of the first flow chamber to close the inlet.

The present invention further provides a method of monitoring the permeability of sheet material, wherein the sheet material is placed across an inlet of a first flow chamber to close said inlet, a gas flow is directed towards said sheet material from a second flow chamber, there being provided a gas-leakage path from said second flow chamber, whereby a significantly greater proportion of the gas flow in said second flow chamber is permitted to leak to atmosphere than that proportion which passes through said sheet material into said first flow chamber, and the gas flow or gas pressure in said second flow chamber is measured.

When paper webs of the tobacco industry are to be monitored, the pressure in the first flow chamber should be very low, for example it should be maintained at a value of not more than about 5 mm W.G. Conveniently the pressure in the first flow chamber is maintained at a value in the region of 1 mm W.G., in which case the pressure in the second flow chamber can be expected to be about 8 mm W.G. Suitably the proportion of the flow of gas, air for example, which passes through the leakage path is at least 90% of the gas flwo entering the second flow chamber.

BRIEF DESCRIPTION OF THE DRAWINGS

In order that the invention may be clearly understood and readily carried into effect, reference will now be made, by way of example, to the accompanying drawing, in which.

DETAILED DESCRIPTION OF THE INVENTION

Figure 1:
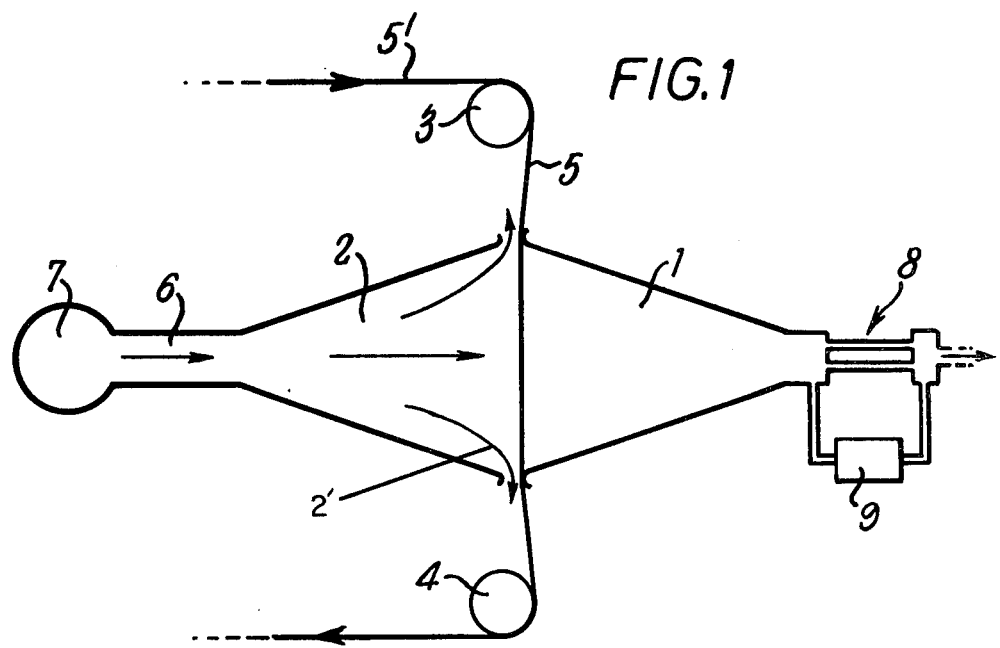
FIG. 1 shows a diagrammatic sectional elevation of a device for monitoring the permeability of a paper-web.

The permeability monitoring device of FIG. 1 comprises a first flow chamber 1 of frusto-conical form and a second flow chamber 2 of similar frusto-conical form. The larger-diameter open ends of the chambers 1 and 2 are in opposed relationship, but are somewhat spaced apart from each other. The spacing may be of the order of 0.4 mm. Mounted above and below the chambers 1 and 2 are guide rollers 3 and 4 about which, in use of the device, a paper web 5, tipping paper for example is trained. The rollers 3 and 4 are so disposed in relation to the inlet end of the chamber 1 that a run of the web 5 is held securely across the inlet of the chamber, thus closing the inlet. The edges of the inlet may be smoothly rounded, as shown, to enhance the closure and facilitate free movement of the web. The web 5 extends from a supply bobbin (not shown) and is caused to be conveyed along the path indicated by arrow 5' in FIG. 1 by drive means (not shown).

The flow chamber 2 communicates via a duct 6 with a source 7 of air under pressure, from which air is supplied to chamber 2 at a constant flow rate. The flow chamber 1 communicates at its downstream end with a multi-capillary laminar-flow element 8. The element 8 comprises four capillary tubes, of which two appear in FIG. 1. For the purpose of measuring the pressure drop across the element 8, a pressure transducer 9 is connected thereacross. The element 8 possesses a linear pressure-drop/flow characteristic and thue measurement of the pressure drop by the transducer 9 provides also a measure of the air flow through the flow chamber 1.

In operation of the device, air at a constant low pressure, 8 mm W.G. for example, is supplied to the flow chamber 2 from the source 7, Approximately 95% of the air supplied to the chamber 2 passes therefrom through the annular gap 2' between the opposed ends of the chamber 1, covered by the web 5, and the chamber 2, which gap provides a leakage path. The remainder of the air flow passes through the paper web 5 into the flow chamber 1, the flow rate in the latter being measured by means of the laminar flow element 8 and pressure transducer 9.

If the paper web 5 is tipping paper, then preferably the web is fed through the permeability monitoring device with the side of the web which is intended to be at the outer side of the cigarette tippings disposed towards the flow chamber 2. In this way it is ensured that the air flow through the web 5 induced by the monitoring device is in the same direction as the air flow through the tippings when the cigarettes are smoked.

It will be appreciated that the permeability monitoring device shown diagrammatically in FIG. 1 possesses the merit of avoiding the use of dust-attracting partial vacuums and of being self-cleaning. Also rubbing contact is avoided at that side of the tipping web which is to be at the outside of the cigarette tippings.

It is advantageous to maintain a very low air pressure regime in the monitoring device, as higher pressures would result in uneconomical waste of air from the leakage path. Furthermore, as the web 5 is moving through the monitoring device at a significant speed, for example 140 m per minute with tipping paper, there will be a tendency for the web to entrain air from within the chamber 1 and, if the pressure in the chamber 1 was too high, for the web 5 to lift away from the mouth of the chamber 1 in the region at which the web 5 passes from the monitoring device. This could produce a leakage path from the chamber 1, resulting in readings from the pressure transducer 9 which were no longer accurately indicative of the permeability of the web 5.

Since the pressure in the flow chamber 1 is of a low value, it is necessary that the means employed to measure the air flow in the chamber 1 should be of adequately low impedance. Flow-measuring means of low impedance other than a laminar flow device, a thermal-effect flow-measuring device for example, could be utilized.

Figure 2:
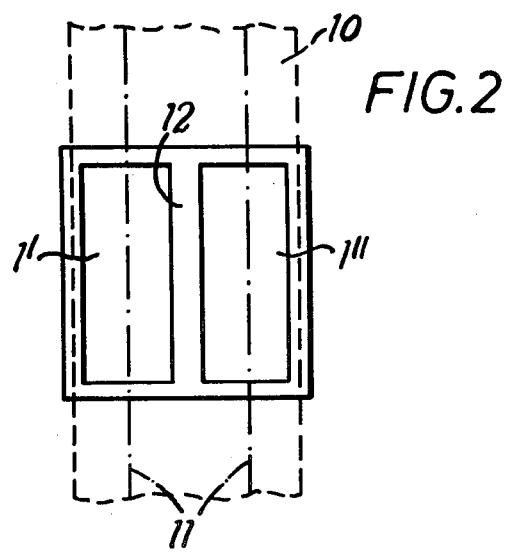
FIG. 2 shows an end view of the inlet of a flow chamber of a modified form of the device shown in FIG. 1.

In FIG. 2 there is shown an inlet-end view of a form of first flow chamber which is suitable for use when the web being monitored, for instance a tipping paper web, has two longitudinal lines of ventilation perforations. Such a web 10 is indicated by broken lines, the two lines of perforations being indicated by chain lines 11. As may be seen from FIG. 2, the modified form of flow chamber comprises a central partition 12. By virtue of the presence of the partition 12, there are in effect two separate flow chambers 1' and 1". With this arrangement, two flow-measuring devices, (each similar to the device 8, 9), one in association with each of the flow chambers 1', 1". Thus, if there occurs a malfunction of on-line perforation devices producing the lines 11 of perforations, this may be detected and a feedback signal to the malfunctioning perforation device provided.

What is claimed is:

1. A device for monitoring the gas-permeability of a sheet material, comprising a first flow chamber having an inlet which, during operation of the device, is closed by the sheet material extending across said inlet, gas-measurement means operable to measure gas flow or gas pressure in said first flow chamber, and a second flow chamber having an outlet whereby a gaseous medium may be directed towards said sheet material, there being provided a gas-leakage path whereby a significantly greater proportion of the gas flow in said second flow chamber is permitted to leak to atmosphere than that proportion which passes through said sheet material into said first flow chamber, the first flow chamber being divided by a partition in the direction of flow and the parts of the divided chamber being connected to separate gas-measurements means.

2. A device according to claim 1, wherein the gas-leakage path is provided by a space between the gas outlet of the second flow chamber and the position of the sheet material in which it extends across the gas inlet of the first flow chamber.

3. A device according to claim 1 or 2, wherein the sheet material is in the form of a web and web-advancing means is provided for feeding the web through the device across the gas inlet of the first flow chamber.

4. A device according to claim 1 or 2, wherein the said flow chambers are of frusto conical form, the inlet of the first chamber being the wider, open, end of that chamber and the outlet of the second chamber being the wider, open, end of that chamber.

5. A device according to claim 1 or 2, wherein the gas-measurement means comprises a pressure transducer connected across a low-impedance lamina-flow device.

6. A method for monitoring the gas permeability of a sheet material, wherein the said material is placed across an inlet of a first flow chamber to close said inlet, a gas flow is directed towards said sheet material from a second flow chamber, there being provided a gas-leakage path from said second flow chamber, whereby a significantly greater proportion of the gas flow in said second flow chamber is permitted to leak to atmosphere than that proportion which passes through said sheet material into said first flow chamber, and the gas flow or gas pressure in said first flow chamber is measured, the pressure in the first flow chamber being low enough to avoid liftoff of the sheet from the inlet of the first flow chamber, at a given speed of the sheet past said inlet.

7. A method according to claim 6, wherein, for a papersheet wrapping material used in the tobacco industry, the pressure in the first flow chamber is maintained at a value not substantially more than 5 mm water gauge.

8. A method according to claim 6, wherein the pressure in the first flow chamber is maintained at a value of substantially 1 mm water gauge.

9. A method according to claim 6 or 7, wherein the pressure in the second flow chamber is substantially 8 mm water gauge.

10. A method according to claim 6 or 7, wherein the proportion of the flow of gas which passes through the leakage path is at least 90% of the gas flow entering the second flow chamber.

* * * * *

UNITED STATES PATENT AND TRADEMARK OFFICE
CERTIFICATE OF CORRECTION

PATENT NO. : 4,471,649

DATED : September 18, 1984

INVENTOR(S) : ARNOLD WILLIAM CRONSHAW

It is certified that error appears in the above-identified patent and that said Letters Patent is hereby corrected as shown below:

Column 2, line 19 "flwo" should be --flow--.

Column 2, line 63 "thue" should be --the--

Signed and Sealed this

Second Day of April 1985

[SEAL]

Attest:

DONALD J. QUIGG

Attesting Officer     Acting Commissioner of Patents and Trademarks